US00PP22076P2

(12) United States Plant Patent
Klemm et al.

(10) Patent No.: US PP22,076 P2
(45) Date of Patent: Aug. 9, 2011

(54) ***CALIBRACHOA* PLANT NAMED 'KLECA09206'**

(50) Latin Name: ***Calibrachoa* hybrid**
Varietal Denomination: KLECA09206

(75) Inventors: Nils Klemm, Stuttgart (DE); Anita Stoever, Ostfildern (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/798,113

(22) Filed: Mar. 30, 2010

(51) Int. Cl.
*A01H 5/00* (2006.01)

(52) U.S. Cl. ..... Plt./413

(58) Field of Classification Search ..... Plt./413
See application file for complete search history.

*Primary Examiner* — Susan McCormick Ewoldt
(74) *Attorney, Agent, or Firm* — Jondle & Associates, P.C.

(57) ABSTRACT

A new *Calibrachoa* plant named 'KLECA09206' particularly distinguished by double, orange flowers with a very early flowering period, is disclosed.

1 Drawing Sheet

Genus and species: *Calibrachoa* hybrid.
Variety denomination: 'KLECA09206'.

BACKGROUND OF THE NEW PLANT

The present invention comprises a new and distinct variety of *Calibrachoa,* botanically known as *Calibrachoa* hybrid and hereinafter referred to by the variety name 'KLECA09206'. The new variety was discovered as a seedling resulting from a cross conducted in June 2006 in Stuttgart, Germany. The female parent was the proprietary *Calibrachoa* plant 'CA060061' (unpatented), while the male parent was the proprietary *Calibrachoa* plant 'Callie Yellow Red' (unpatented).

The new variety was first propagated via vegetative cuttings in May 2007 in Stuttgart, Germany and has been asexually reproduced by vegetative cuttings and in-vitro propagation in Stuttgart, Germany for more than 35 generations. The present invention has been found to retain its distinctive characteristics through successive asexual propagations via vegetative cuttings.

Plant Breeder's Rights for this variety have not been applied for. 'KLECA09206' has not been made publicly available more than one year prior to the filing date of this application.

SUMMARY OF THE INVENTION

The following are the most outstanding and distinguishing characteristics of this new variety when grown under normal horticultural practices in Stuttgart, Germany.

1. Double, small-sized orange flowers;
2. A semi-upright form and growth habit; and
3. A very early flowering period.

DESCRIPTION OF THE PHOTOGRAPH

This new *Calibrachoa* plant is illustrated by the accompanying photograph which shows flowers and foliage of the plant. The colors shown are as true as can be reasonably obtained by conventional photographic procedures. The photograph was taken in May 2009 of a 5-month old *Calibrachoa* plant, grown in a glass greenhouse in Stuttgart, Germany.

DESCRIPTION OF THE NEW VARIETY

The following detailed descriptions set forth the distinctive characteristics of 'KLECA09206'. The data which defines these characteristics were collected from asexual reproductions carried out in Stuttgart, Germany. The plant history was taken in May 2009 on 5-month old plants which were planted as rooted cuttings in an 11 centimeter pot and then grown in a glass greenhouse. The plants had one terminal pinch after potting. Color readings were taken under natural light. Color references are primarily to The R.H.S. Colour Chart of The Royal Horticultural Society of London (R.H.S.), Fifth Edition (2007).

DETAILED BOTANICAL DESCRIPTION OF THE NEW PLANT

Classification:
- *Family.*—Solanaceae.
- *Botanical.*—*Calibrachoa* sp.
- *Common.*—*Calibrachoa* Hybrid.

Parentage:
- *Female.*—The proprietary *Calibrachoa* plant 'CA060061' (unpatented).
- *Male.*—The proprietary *Calibrachoa* plant 'Callie Yellow Red' (unpatented).

Growth:
- *Form.*—Semi-upright.
- *Habit.*—Semi-upright.
- *Height* (*measured from the top of the soil*).—7.0 cm.
- *Width* (*horizontal plant diameter*).—15.0 cm.
- *Time to produce a finished flowering plant.*—8 weeks.
- *Outdoor plant performance.*—Continuously flowering, healthy, good rain tolerance.
- *Time to initiate and develop roots.*—18 days.
- *Root description.*—Moderate density, moderate branching, white roots.

Stems:
- *Length of basal branches.*—7.0 cm.
- *Internode length.*—1.0 cm.

*Diameter of branches* (*from midpoint*).—4.0 cm to 6.0 cm.
*Color.*—RHS 144B.
*Texture.*—Smooth.
*Anthocyanin.*—No.
*Pedicel.*—Color: RHS N137D. Length: 1.5 cm. Diameter: 0.1 cm. Texture: Smooth.

Leaves:
*Arrangement.*—Alternate.
*Size.*—Length: 2.0 cm to 2.5 cm. Width: 0.5 cm.
*Shape.*—Lanceolate to elliptic.
*Apex.*—Acute.
*Base.*—Attenuate.
*Margin.*—Entire.
*Color* (*immature leaves*).—Upper surface: RHS N138B. Lower surface: RHS N146B.
*Color* (*mature leaves*).—Upper surface: RHS 138B. Lower surface: RHS 138C.
*Texture* (*both upper and lower surfaces*).—Smooth.
*Venation.*—Pinnate.
*Venation color* (*both upper and lower surfaces*).—RHS 144A.
*Petioles.*—Absent.

Flower bud:
*Shape.*—Irregular to oblong.
*Size.*—Length: 1.5 cm. Diameter: 0.5 cm.
*Color at tight bud.*—RHS N187.

Inflorescence:
*Blooming habit.*—Continuous flowering during summertime.
*Inflorescence type.*—Double flower, determinate inflorescence.
*Floret type.*—Double flowers.
*Lastingness of individual blooms on the plant.*—7 days.
*Fragrance.*—Absent.

Flowers:
*Immature flower.*—Diameter: Horizontal: 1.5 cm. Vertical: 1.5 cm. Color: Upper surface: RHS 29A and RHS 47A. Lower surface: RHS 31D and RHS 53D.
*Mature flower.*—Diameter: Horizontal: 1.7 cm. Vertical: 1.5 cm. Color: Upper surface: RHS N34B and RHS 31A. Lower surface: RHS 34D and RHS 53A.
*Corolla tube.*—Color inside: RHS 12A. Color outside: RHS 12B. Tube length: 1.3 cm. Texture (outside and inside): Smooth.
*Petals.*—Apex: Obverse. Base: Open, fused into the tube. Margin: Entire. Waviness of petals: Very weak. Lobation: Weak. Texture (both upper and lower surfaces): Smooth.
*Sepals.*—Calyx (composition): Actinomorphic. Shape: Lanceolate to elliptic. Apex: Acute. Base: Open, tube fused into the base. Margin: Entire. Length: 1.0 cm. Width: 0.1 cm. Color: Upper surface: RHS 138A. Lower surface: RHS 138B. Texture (both upper and lower surfaces): Smooth.

Reproductive organs:
*Stamens.*—Absent.
*Pollen quantity.*—None.
*Pistils.*—Number: 1. Length: 0.9 cm. Diameter: 0.11 cm. Stigma color: RHS 149B. Style color: RHS 149C.

Fruit and seed set: No fruit or seed set observed.

Disease and insect resistance: No particular resistance or susceptibility has been observed.

COMPARISON WITH PARENTAL AND COMMERCIAL VARIETIES

'KLECA09206' differs from the female parent, the proprietary *Calibrachoa* plant 'CA060061' (unpatented), in that 'KLECA09206' has orange flowers, while 'CA060061' has light rose flowers.

'KLECA09206' differs from the male parent, the proprietary *Calibrachoa* plant 'Callie Yellow Red' (unpatented), in that 'KLECA09206' has double flowers, while 'Callie Yellow Red' has single flowers.

'KLECA09206' differs from the commercial variety 'KLECA08187' (U.S. Plant patent application Ser. No. 21,020) in that 'KLECA09206' has double, small-sized flowers, while 'KLECA08187' has single, medium to large-sized flowers.

We claim:

1. A new and distinct variety of *Calibrachoa* hybrid plant named 'KLECA09206' as shown and described herein.

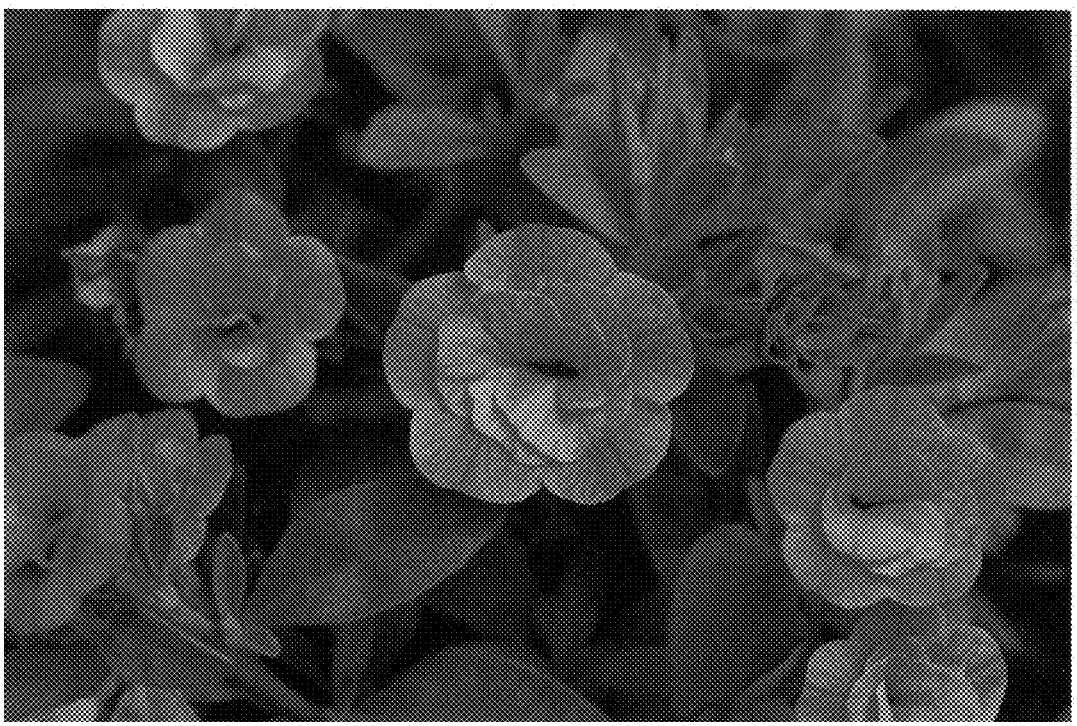

* * * * *